United States Patent [19]

Harashima

[11] Patent Number: 5,328,683
[45] Date of Patent: Jul. 12, 1994

[54] WATER REPELLENT AND METHOD OF PREPARATION

[75] Inventor: Asao Harashima, Tokyo, Japan

[73] Assignee: Dow Corning Toray Silicone Co., Ltd., Tokyo, Japan

[21] Appl. No.: 85,809

[22] Filed: Jul. 6, 1993

Related U.S. Application Data

[62] Division of Ser. No. 19,413, Feb. 18, 1993.

[30] Foreign Application Priority Data

Feb. 28, 1992 [JP] Japan ................................ 4-079050

[51] Int. Cl.$^5$ ............................................. A61K 7/021
[52] U.S. Cl. ...................................... 424/63; 424/401; 523/212
[58] Field of Search ................... 424/63, 401; 523/212

[56] References Cited

U.S. PATENT DOCUMENTS

| 4,753,977 | 6/1988 | Merrill | 524/588 |
| 5,219,560 | 6/1993 | Suzuki et al. | 424/401 |

FOREIGN PATENT DOCUMENTS

61-30512  2/1986  Japan ..................................... 424/63

Primary Examiner—John C. Bleutge
Assistant Examiner—Mark D. Sweet
Attorney, Agent, or Firm—Jim L. DeCesare

[57] ABSTRACT

A water repellent powdered material and a method of making the powder in which the powdered material is mixed with an organic solvent solution of a triorganosiloxysilicic acid having the formula $(R_3SiO_{\frac{1}{2}})_2\cdot nSiO_2$ in which R is a monovalent hydrocarbon radical such as alkyl, aryl, and alkenyl; and n is an integer having a value of one to five; with the acid being present in an amount of from 0.1 to 20 parts by weight per one hundred parts by weight of the powdered material. The powder can be used to formulate cosmetic foundations.

4 Claims, No Drawings

WATER REPELLENT AND METHOD OF PREPARATION

This is a divisional of copending application Ser. No. 08/019,413 filed on Feb. 19, 1993 pending.

BACKGROUND OF THE INVENTION

The present invention relates to a water-repellent powder and to a method for the preparation thereof. More specifically, the present invention relates to a water-repellent powder comprising powder whose surface is coated with triorganosiloxysilicic acid and to a method for the preparation thereof.

Due to their excellent flowability, dispersibility, and lipophilicity, water-repellent powders are widely employed for cosmetics, pharmaceuticals, organic resins, paints, coatings, and magnetic material. Known water-repellent powders include, for example, water-repellent powders prepared by treating the surface of a powder with dimethyldichlorosilane (Japanese Patent Application Laid Open [Kokai or Unexamined] Number Sho 50-51494 [51,494/1975]), water-repellent powders prepared by treating the surface of a powder with hexamethyldisilazane (Japanese Patent Application Laid Open Numbers Sho 50-51494 and Sho 53-9297 [9,297/1978]), and water-repellent powders prepared by treating the surface of a powder with methylhydrogenpolysiloxane (Japanese Patent Publication [Kokoku] Number Hei 1-54381 [54,381/1989]).

However, the water-repellent powders disclosed in Japanese Patent Application Laid Open Numbers Sho 50-51494 and Sho 53-9297 contain residual hydrogen chloride or ammonia (reaction by-products), and this places limitations on the application of these water-repellent powder products in cosmetics, and organic resins. The water-repellent powder disclosed in Japanese Patent Publication Number Hei 1-54381 evolves hydrogen during its storage, which raises the risk of explosion during the storage of this type of powder. Moreover, when this water-repellent powder is employed in cosmetics, it can cause such problems as a change in the color of the cosmetic, foundation caking, tarnishing mirrors positioned over the foundation. When the water-repellent powder disclosed in Japanese Patent Publication Number Hei 1-54381 is employed in organic resins, it evolves hydrogen gas when the organic resin is molded and/or with the simple passage of time. This causes the appearance of bubbles in the organic resin, with a resulting substantial decline in the strength of the organic resin. Finally, the use of this type of water-repellent powder in inks is associated with a strong tendency for the ink pigment to aggregate.

The preparative methods for the water-repellent powders disclosed in the aforementioned patents require the careful removal of reaction by-products that are released during the manufacturing process, e.g., hydrogen chloride, ammonia, or hydrogen, and this requirement results in each case in a poor productivity.

SUMMARY OF THE INVENTION

The present invention takes as its objects the introduction of highly storage-stable water-repellent powder that is free of residual reaction by-products and the introduction of a highly productive method for the preparation of such a water-repellent powder.

DETAILED DESCRIPTION OF THE INVENTION

The present invention relates both to water-repellent powder comprising powder whose surface has been treated by triorganosiloxysilicic acid and to a method for the preparation of water-repellent powder wherein said method consists of mixing a powder and an organic solvent solution of triorganosiloxysilicic acid, wherein the triorganosiloxysilicic acid is present at 0.1 to 20 weight parts per 100 weight parts powder, and subsequently removing said organic solvent.

No specific restrictions are placed on the powder used as the base material of the water-repellent powder of the present invention, and various types of powders are useable. This powder is exemplified by inorganic pigments such as ultramarine blue, prussian blue, manganese violet, titanium-coated mica, bismuth oxychloride, iron oxide, iron hydroxide, titanium dioxide, low-order titanium dioxide, and chromium hydroxide; metal oxides such as magnesium oxide, calcium oxide, aluminum oxide, silica, iron oxide, (yellow) iron oxide, (red) iron oxide, (black) iron oxide, titanium oxide, low-order titanium oxide, zirconium oxide, chromium oxide, manganese oxide, cobalt oxide, and nickel oxide; metal hydroxides such as magnesium hydroxide, calcium hydroxide, aluminum hydroxide, chromium hydroxide, and iron hydroxide; composite oxides and composite hydroxides such as silica alumina, iron titanate, cobalt titanate, lithium cobalt titanate, and cobalt aluminate; organic pigments such as Red Nos. 3, 104, 106, 201, 202, 204, 205, 206, 207, 220, 226, 227, 228, 230, and 405, Orange Nos. 203, 204, and 205, Yellow Nos. 4, 5, 205, and 401, and Blue Nos. 1 and 404; organic resin powders such as the powders of nylon resins, polystyrene resins, acrylic resins, methacrylic resins, polyester resins, titanium-coated nylon resins, and titanium-coated polyester resins; pearlescent powders such as mica/titanium composite powder, mica/iron oxide composite powder, bismuth oxychloride, guanine, titanium nitride oxide, low-order titanium oxide, and titanium-coated mica; phyllosilicate minerals such as kaolin, montmorillonite, illite, chlorite, and serpentine; tectosi licate minerals such as zeolites; silicate minerals such as pyrophyllite, talc, chlorite, chrysotile, antigorite, lizardite, kaolinite, dickite, nacrite, hallosite, montmorillonite, nontronite, saponite, sauconite, bentonite, natrolite, heulandite, stilbite, mesolite, scolecite, thomsonite, epistilbite, analcime, harmotome, phillipsite, chabazite, and gmelinite; porous materials such as pyrophyllite, talc, chlorite, chrysotile, antigorite, lizardite, kaolinite, dickite, nacrite, hallosite, montmorillonite, nontronite, saponite, sauconite, bentonite, natrolite, mesolite, scolecite, thomsonite, heulandite, stilbite, epistilbite, analcime, harmotome, phillipsite, chabazite, gmelinite, muscovite, phlogopite, biotite, sericite, lepidomelane, lepidolite, lithia mica, zinnwaldite, and paragonite; carbon; metals such as iron, cobalt, nickel, copper, zinc, aluminum, chromium, titanium, zirconium, molybdenum, silver, indium, tin, antimony, tungsten, platinum, gold, and their alloys; biopolymers such as keratins (e.g., hair, fur, feather, horn, and hoof); collagen, cellulose, hemicellulose, pectin, chitin, chitosan, alginic acid, chondroitin, nucleic acids, and peptidoglucans; and micas such as muscovite, phlogopite, biotite, sericite, lepidomelane, lepidolite, lithia mica, zinnwaldite, and paragonite as well as the composite powders of these micas. The preceding can be used singly or in mixtures of two or more types. The particle size of the powder is not specifically restricted, and various types of powders having various particle sizes can be used. However, powder with an average particle size in the range of 0.05 to 500 micrometers is preferred, and powder with an average particle size in the range of 0.05 to 100 micrometers is more preferred.

The triorganosiloxysilicic acid is a co-condensate that is essentially composed of the $SiO_2$ unit and the $R_3SiO_{\frac{1}{2}}$ unit. In addition to the $R_3SiO_{\frac{1}{2}}$ and $SiO_2$ units, it may also contain small quantities of $R_2SiO_{2/2}$ and $RSiO_{3/2}$ units, but a preferred triorganosiloxysilicic acid has the formula $(R_3SiO_{\frac{1}{2}})_2nSiO_2$ in which R is a monovalent hydrocarbon group and n is a number with a value of 1 to 5. The group R in the preceding formula comprises monovalent hydrocarbon groups, and R is exemplified by alkyl groups such as methyl, ethyl, and propyl; aryl groups such as phenyl, and tolyl; and alkenyl groups such as vinyl, allyl, and hexenyl. However, R is preferably methyl due to the excellent properties of the corresponding water-repellent powder. The subscript n should be a number with a value of 1 to 5. When n is less than 1, the triorganosiloxysilicic acid will be soluble in organic solvents, but the corresponding water-repellent powder will have a strong tendency to aggregate and thus will have a poor flowability. When n exceeds 5, the triorganosiloxysilicic acid will be poorly soluble in organic solvents with tile result that the water-repellent treatment of the powder surface will be inhomogeneous. The molecular weight of the triorganosiloxysilicic acid is not specifically restricted, but preferred molecular weights fall in the range of 500 to 10,000.

Methods for synthesis of the triorganosiloxysilicic acid are specifically exemplified as follows:

(a) water glass and triorganochlorosilane or hexaorganodisilazane are reacted with heating in an aromatic solvent/water mixture followed by extractive drying; or (b) trimethylchlorosilane and tetraethyl silicate are reacted with heating in an aromatic solvent/water mixture followed by extractive drying.

The triorganosiloxysilicic acid is preferably soluble in organic solvent in order to facilitate handling. Said organic solvents are not specifically restricted and are exemplified by alcohol solvents such as ethyl alcohol, isopropyl alcohol, and butyl alcohol; ketone solvents such as acetone, methyl ethyl ketone, and methyl isobutyl ketone; ester solvents such as ethyl acetate, and butyl acetate; chlorinated solvents such as chloroform, carbon tetrachloride, dichloromethane, and trichloroethylene; aromatic solvents such as toluene, xylene, and benzene; aliphatic solvents such as hexane, heptane, ligroin, mineral terpene, and rubber volatile oil; and silicone oils such as cyclic silicones, polydimethylsiloxanes, and polyether-modified silicones.

The preparative method of the present invention is characterized by first mixing a powder (A) with an organic solvent solution of triorganosiloxysilicic acid (B) and then removing the organic solvent.

The triorganosiloxysilicic acid should be used in the preparative method of the present invention at 0.1 to 20 weight parts per 100 weight parts powder. The use of less than 0.1 weight parts triorganosiloxysilicic acid per 100 weight parts powder will not produce a satisfactorily water-repellent powder. The use of more than 20 weight parts adversely affects the flowability of the water-repellent powder product.

The method by which the powder surface is coated with triorganosiloxysilicic acid is not specifically restricted by the preparative method of the present invention. Specific examples in this regard consist of immersing the powder in the organic solvent solution of the triorganosiloxysilicic acid and spraying the organic solvent solution of the triorganosiloxysilicic acid onto the stirred powder. After the surface of the powder has been coated as described above with the organic solvent solution of triorganosiloxysilicic acid, removal of the organic solvent then affords the water-repellent powder of the present invention. The method for removing the organic solvent is again not specifically restricted, and any method can be employed. Examples of preferred methods are drying in an oven and spray drying.

Because the surface of the water-repellent powder is coated with triorganosiloxysilicic acid, the water-repellent powder of the present invention does not undergo timewise changes in quality, odor, or color during powder storage and also exhibits an excellent flowability and dispersibility. As a consequence, the water-repellent powder of the present invention can be employed in such fields as cosmetics, pharmaceuticals, organic resins, paints, inks, art supplies, decorations, perfumes, magnetic materials, and medical supplies.

The present invention will be explained in the following illustrative examples. The water contact angle was measured at 25° C.

2 kg mica powder (average particle size=5.2 micrometers) was placed in a Henschel mixer and sprayed with 133 g 30 weight % decamethylcyclopentasiloxane solution of trimethylsiloxysilicic acid composed of $(CH_3)_3SiO_{\frac{1}{2}}$ and $SiO_2$ units in a $(CH_3)_3SiO_{\frac{1}{2}} : SiO_2$ ratio of 1:1.1 while stirring at 1,000 rpm. After stirring for 10 minutes, the mica powder was removed and dried in an oven at 100° C. to give a water-repellent mica powder. This water-repellent mica powder was compression-molded under a pressure of 200 kg/cm². A 50 microliter water droplet was placed on the surface of the molding, and the water contact angle was measured 3 minutes after the droplet had been placed on the surface. In addition, the powder was degassed and sealed into a polyethylene bag which was subsequently held in an oven at 50° C. for 1 month. Swelling of the bag was then inspected. These results are reported in Table 1.

COMPARISON EXAMPLE 1

2 kg mica powder (average particle size=5.2 micrometers) was placed in a Henschel mixer and sprayed with 133 g 30 weight % decamethylcyclopentasiloxane solution of methylhydrogenpolysiloxane with the formula

$(CH_3)_3SiO((CH_3)HSiO)_{40}Si(CH_3)_3$ while stirring at 1,000 rpm. After stirring for 10 minutes, the mica powder was removed and dried in an oven at 100° C. to give a water-repellent mica powder. This water-repellent mica powder was compression-molded under a pressure of 200 kg/cm². A 50 microliter water droplet was placed on the surface of the molding, and the water contact angle was measured 3 minutes after the droplet had been placed on the surface. In addition, the powder was degassed and sealed into a polyethylene bag which was subsequently held in an oven at 50° C. for 1 month. Swelling of the bag was then inspected. These results are also reported in Table 1.

TABLE 1

|  | Example 1 | Comparison Example 1 |
|---|---|---|
| water contact angle in degrees | 130 | 130 |
| Appearance of bag | no change | expanded |

EXAMPLE 2

2 kg titanium oxide powder (average particle size=0.5 micrometers) was placed in a Henschel mixer and sprayed with 50 g 30 weight % decamethylcyclopentasiloxane solution of trimethylsiloxysilicic acid composed of $(CH_3)_3SiO_{\frac{1}{2}}$ and $SiO_2$ units in a $(CH_3)_3SiO_{\frac{1}{2}}$ : $SiO_2$ ratio of 1:1.1 while stirring at 1,000 rpm. After stirring for 10 minutes, the titanium oxide powder was removed and dried in an oven at 100° C. to give a water-repellent titanium oxide powder. This water-repellent titanium oxide powder was compression-molded under a pressure of 200 kg/cm². A 50 microliter water droplet was placed on the surface of the molding, and the water contact angle was measured 3 minutes after the droplet had been placed on the surface. In addition, the powder was degassed and sealed into a polyethylene bag which was subsequently held in an oven at 50° C. for 1 month. Swelling of the bag was then inspected. These results are reported in Table 2.

COMPARISON EXAMPLE 2

2 kg titanium oxide powder (average particle size=0.5 micrometers) was placed in a Henschel mixer and sprayed with 133 g 30 weight % decamethylcyclopentasiloxane solution of methylhydrogenpolysiloxane with the formula

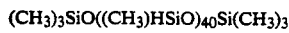

while stirring at 1,000 rpm. After stirring for 10 minutes, the titanium oxide powder was removed and dried in an oven at 100° C. to give a water-repellent titanium oxide powder. This water-repellent titanium oxide powder was compression-molded under a pressure of 200 kg/cm². A 50 microliter water droplet was placed on the surface of the molding, and the water contact angle was measured 3 minutes after the droplet had been placed on the surface. In addition, the powder was degassed and sealed into a polyethylene bag which was subsequently held in an oven at 50° C. for 1 month. Swelling of the bag was then inspected. These results are also reported in Table 2.

TABLE 2

|  | Example 2 | Comparison Example 2 |
|---|---|---|
| water contact angle in degrees | 115 | 115 |
| appearance of bag | no change | expanded |

EXAMPLE 3

2 kg nylon powder (average particle size=4.0 micrometers) was placed in a Henschel mixer and sprayed with 200 g 30 weight % decamethylcyclopentasiloxane solution of trimethylsiloxysilicic acid composed of $(CH_3)_3SiO_{\frac{1}{2}}$ and $SiO_2$ units in a $(CH_3)_3SiO_{\frac{1}{2}}$:$SiO_2$ ratio of 1:1.1 while stirring at 1,000 rpm. After stirring for 10 minutes, the nylon powder was removed and dried in an oven at 100° C. to give a water-repellent nylon powder. This water-repellent nylon powder was compression-molded under a pressure of 200 kg/cm². A 50 microliter water droplet was placed on the surface of the molding, and the water contact angle was measured 3 minutes after the droplet had been placed on the surface. In addition, the water-repellent nylon powder was degassed and sealed into a polyethylene bag. The development of odor was scored after the bag had been held in an oven at 50° C. for 1 month. These results are reported in Table 3.

COMPARISON EXAMPLE 3

2 kg nylon powder (average particle size=4.0 micrometers) was placed in a Henschel mixer and sprayed with 200 g 30 weight % decamethylcyclopentasiloxane solution of hexamethyldisilazane while stirring at 1,000 rpm. After stirring for 10 minutes, the nylon powder was removed and dried in an oven at 100° C. to give a water-repellent nylon powder. This water-repellent nylon powder was compression-molded under a pressure of 200 kg/cm². A 50 microliter water droplet was placed on the surface of the molding, and the water contact angle was measured 3 minutes after the droplet had been placed on the surface. In addition, the water-repellent nylon powder was degassed and sealed into a polyethylene bag. The development of odor was scored after the bag had been held in an oven at 50° C. for 1 month. These results are also reported in Table 3.

TABLE 3

|  | Example 3 | Comparison Example 3 |
|---|---|---|
| water contact angle in degrees | 108 | 108 |
| development of odor? | on change | ammonia odor |

EXAMPLE 4

2 kg talc powder (average particle size=3.0 micrometers) was placed in a Henschel mixer and sprayed with 500 g 30 weight % methylene chloride solution of trimethylsiloxysilicic acid composed of $(CH_3)_3SiO_{\frac{1}{2}}$ and $SiO_2$ units in a $(CH_3)_3SiO_{\frac{1}{2}}$:$SiO_2$ ratio of 1:1.1 while stirring at 1,000 rpm. After stirring for 10 minutes, the talc powder was removed and dried in an oven at 100° C. to give a water-repellent talc powder. This water-repellent talc powder was compression-molded under a pressure of 200 kg/cm². A 50 microliter water droplet was placed on the surface of the molding, and the water contact angle was measured 3 minutes after the droplet had been placed on the surface. In addition, the water-repellent talc powder was degassed and sealed into a polyethylene bag which was subsequently held in an oven at 50° C. for 1 month. Swelling of the bag was then inspected. These results are reported in Table 4.

COMPARISON EXAMPLE 4

2 kg talc powder (average particle size =3.0 micrometers) was placed in a Henschel mixer and sprayed with 500 g 30 weight % methylene chloride solution of methylhydrogenpolysiloxane with the formula

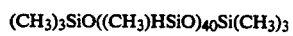

while stirring at 1,000 rpm. After stirring for 10 minutes, the talc powder was removed and dried in an oven at 100° C. to give a water-repellent talc powder. This water-repellent talc powder was compression-molded under a pressure of 200 kg/cm². A 50 microliter water droplet was placed on the surface of the molding, and the water contact angle was measured 3 minutes after the droplet had been placed on the surface. In addition, the water-repellent talc powder was degassed and sealed into a polyethylene bag which was subsequently held in an oven at 50° C. for 1 month. Swelling of the bag was then inspected. These results are also reported in Table 4.

TABLE 4

|  | Example 4 | Comparison Example 4 |
|---|---|---|
| water contact angle in degrees | 114 | 108 |
| appearance of bag | no change | expanded |

EXAMPLE 5

2 kg iron oxide red powder (average particle size=0.5 micrometers) was placed in a Henschel mixer and sprayed with 133 g 30 weight % decamethylcyclopentasiloxane solution of trimethylsiloxysilicic acid composed of $(CH_3)_3SiO_{\frac{1}{2}}$ and $SiO_2$ units in a $(CH_3)_3SiO_{\frac{1}{2}}:SiO_2$ ratio of 1:1.1 while stirring at 1,000 rpm. After stirring for 10 minutes, the iron oxide red powder was removed and dried in an oven at 100° C. to give a water-repellent iron oxide red powder. This water-repellent iron oxide red powder was compression-molded under a pressure of 200 kg/cm². A 50 microliter water droplet was placed on the surface of the molding, and the water contact angle was measured 3 minutes after the droplet had been placed on the surface. In addition, the water-repellent iron oxide red powder was degassed and sealed into a polyethylene bag which was subsequently held in an oven at 50° C. for 1 month. Swelling of the bag was then inspected. These results are reported in Table 5.

COMPARISON EXAMPLE 5

2 kg iron oxide red powder (average particle size=0.5 micrometers) was placed in a Henschel mixer and sprayed with 133 g 30 weight % decamethylcyclopentasiloxane solution of methylhydrogenpolysiloxane with the formula $$(CH_3)_3SiO((CH_3)HSiO)_{40}Si(CH_3)_3$$

while stirring at 1,000 rpm. After stirring for 10 minutes, the iron oxide red powder was removed and dried in an oven at 100° C. to give a water-repellent iron oxide red powder. This water-repellent iron oxide red powder was compression-molded under a pressure of 200 kg/cm². A 50 microliter water droplet was placed on the surface of the molding, and the water contact angle was measured 3 minutes after the droplet had been placed on the surface. In addition, the water-repellent iron oxide red powder was degassed and sealed into a polyethylene bag which was subsequently held in an oven at 50° C. for 1 month. Swelling of the bag was then inspected. These results are also reported in Table 5.

TABLE 5

|  | Example 5 | Comparison Example 5 |
|---|---|---|
| water contact angle in degrees | 103 | 100 |
| appearance of bag | no change | expanded |

APPLICATION EXAMPLE 1

The following were mixed with heating: 10 weight parts beeswax, 5 weight parts carnauba wax, 10 weight parts microcrystalline wax, 1 weight part white vaseline, 10 weight parts liquid paraffin, 10 weight parts dimethylpolysiloxane of a viscosity of 5 centistokes, and 20 weight parts of a water-repellent powder mixture prepared by blending the water-repellent mica powder, water-repellent titanium oxide powder, water-repellent talc powder, and water-repellent iron oxide red powder respectively prepared in Examples 1, 2, 4, and 5 in a ratio of 10:10:10:1. Ten grams of the resulting mixture was sampled into a powder foundation refill and set in a compression press (30 kg/cm²) to give a powder foundation. A mirror was placed on the powder foundation, and held in an oven at 50° C. for 1 month. After one month, the surface condition of the powder foundation and tarnishing of the mirror placed on the powder foundation were inspected. These results are reported in Table 6.

REFERENCE EXAMPLE 1

The following were mixed with heating: 10 weight parts beeswax, 5 weight parts carnauba wax, 10 weight parts microcrystalline wax, 1 weight part white vaseline, 10 weight parts liquid paraffin, 10 weight parts dimethylpolysiloxane of a viscosity of 5 centistokes, and 20 weight parts of a water-repellent powder mixture prepared by blending the water-repellent mica powder, water-repellent titanium oxide powder, water-repellent talc powder, and water-repellent iron oxide red powder respectively prepared in Comparison Examples 1, 2, 4, and 5 in a ratio of 10:10:10:1. Ten grams of the resulting mixture was sampled into a powder foundation refill and set in a compression press (30 kg/cm²) to give a powder foundation. A mirror was placed on the powder foundation, and this assembly was held in an oven at 50° C. for one month. After one month, the surface condition of the powder foundation and tarnishing of the mirror placed on the powder foundation were inspected. These results are also reported in Table 6.

TABLE 6

|  | Application Example 1 | Reference Example 1 |
|---|---|---|
| surface condition | uniform and smooth | the color was uneven and caking had occurred |
| mirror surface | no change | tarnished |

The water-repellent powder of the present invention is characteristically free of residual reaction by-products and has an excellent stability over time.

Other variations and modifications may be made in the compounds, compositions, and methods described herein without departing from the essential features and concepts of the present invention. The forms of the invention described herein are exemplary only and are not intended as limitations on the scope of the invention as defined in the appended claims.

That which is claimed is:

1. A cosmetic foundation comprising a wax, a liquid paraffin, a dimethylpolysiloxane, and a water repellent powder made by (i) mixing a powdered material with an organic solvent solution of a triorganosiloxy silicic acid having the formula $(R_3SiO_{178})_nSiO_2$ in which R is a monovalent hydrocarbon radical selected from the group consisting of alkyl, aryl, and alkenyl; and n is an integer having a value of one to five; the triorganosiloxy silicic acid being present in an amount of from 0.1 to 20 parts by weight per one hundred parts by weight of the powdered material; the triorganosiloxy silicic acid being prepared by reacting water glass and a hexaorganodisilizane with heating in an aromatic solvent/water mixture followed by extractive drying; and (ii) removing the solvent.

2. A cosmetic according to claim 1 in which the powdered material has an average particle size in the range of 0.05 to 500 micrometers.

3. A cosmetic according to claim 1 in which the triorganosiloxy silicic acid has a molecular weight in the range of 500 to 10,000.

4. A cosmetic according to claim 3 in which the triorganosiloxy silicic acid ($R_3SiO_{\frac{1}{2}}$) units and $SiO_2$ units in a ratio of 1.0 to 1.1.

* * * * *

UNITED STATES PATENT AND TRADEMARK OFFICE
CERTIFICATE OF CORRECTION

PATENT NO. : 5,328,683

DATED : July 12, 1994

INVENTOR(S) : Asao Harashima

It is certified that error appears in the above-identified patent and that said Letters Patent is hereby corrected as shown below:

Column 8 line 62 "$R_3SiO_{178}$" should read --- $R_3SiO_{1/2}$ ---

Signed and Sealed this

Twenty-seventh Day of September, 1994

Attest:

BRUCE LEHMAN

Attesting Officer  Commissioner of Patents and Trademarks